United States Patent
Kori et al.

(10) Patent No.: US 11,267,937 B2
(45) Date of Patent: *Mar. 8, 2022

(54) METHOD FOR PRODUCING DIHYDROXYNAPHTHALENE CONDENSATE AND DIHYDROXYNAPHTHALENE CONDENSATE

(71) Applicant: SHIN-ETSU CHEMICAL CO., LTD., Tokyo (JP)

(72) Inventors: Daisuke Kori, Joetsu (JP); Seiichiro Tachibana, Joetsu (JP); Tsutomu Ogihara, Joetsu (JP); Satoru Kitano, Takasaki (JP); Yukio Abe, Takasaki (JP); Fumihiro Hatakeyama, Takasaki (JP); Taiki Kobayashi, Isesaki (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 232 days.

This patent is subject to a terminal disclaimer.

(21) Appl. No.: 16/225,275

(22) Filed: Dec. 19, 2018

(65) Prior Publication Data
US 2019/0194391 A1 Jun. 27, 2019

(30) Foreign Application Priority Data
Dec. 26, 2017 (JP) .............. JP2017-248937

(51) Int. Cl.
*C08G 65/34* (2006.01)
*B01D 15/08* (2006.01)
(Continued)

(52) U.S. Cl.
CPC .............. *C08G 65/34* (2013.01); *B01D 15/08* (2013.01); *B01J 20/08* (2013.01); *C07C 37/82* (2013.01);
(Continued)

(58) Field of Classification Search
None
See application file for complete search history.

(56) References Cited

U.S. PATENT DOCUMENTS

| 5,491,268 A * | 2/1996 | Cipullo .................. C07C 37/82 568/749 |
| 2012/0184103 A1 | 7/2012 | Ogihara et al. |
| 2016/0056047 A1* | 2/2016 | Kori .................... H01L 21/0271 524/592 |

FOREIGN PATENT DOCUMENTS

| EP | 2476713 A1 | 7/2012 |
| JP | 2007-099741 A | 4/2007 |
| WO | 2009/119201 A1 | 10/2009 |

OTHER PUBLICATIONS

J. Abe et al. "SUB-55-NM Etch Process Using Stacked-Mask Process". 2005 Dry Process International Symposium, pp. 11.

(Continued)

*Primary Examiner* — Randy P Gulakowski
*Assistant Examiner* — Ha S Nguyen
(74) *Attorney, Agent, or Firm* — Oliff PLC

(57) ABSTRACT

The invention provides: a dihydroxynaphthalene condensate which suppresses soft particle generation and is suitably usable for a composition excellent in filterability; and a method for producing the dihydroxynaphthalene condensate. In the method for producing a dihydroxynaphthalene condensate, dihydroxynaphthalene to be used has a sulfur element content of 100 ppm or less in terms of mass among constituent elements. The dihydroxynaphthalene and a condensation agent are condensed in presence of an acid or a base to produce the dihydroxynaphthalene condensate.

20 Claims, 1 Drawing Sheet

(51) Int. Cl.
*B01J 20/08* (2006.01)
*C07C 37/82* (2006.01)
*C08G 8/04* (2006.01)
*C08G 8/20* (2006.01)
*G03F 7/09* (2006.01)
*C07C 39/14* (2006.01)
*C08G 10/04* (2006.01)
*C08L 61/06* (2006.01)

(52) U.S. Cl.
CPC ............. *C08G 8/04* (2013.01); *C08G 8/20* (2013.01); *G03F 7/091* (2013.01); *G03F 7/094* (2013.01); *B01D 2257/30* (2013.01); *C07C 39/14* (2013.01)

(56) References Cited

OTHER PUBLICATIONS

Jun. 7, 2019 Search Report issued in European Patent Application No. 19150061.0.
James T. Hall et al. "Adsorption and Orientation of Sulfonic Acids on Aluminum Oxide: A Tunneling Spectroscopy Study". Surface Science, North-Holland, Amsterdam, vol. 71, No. 1, Jan. 2, 1978, pp. 1-14.
May 25, 2021 Office Action issued in Japanese Patent Application No. 2017-248937.

\* cited by examiner

[FIG. 1]
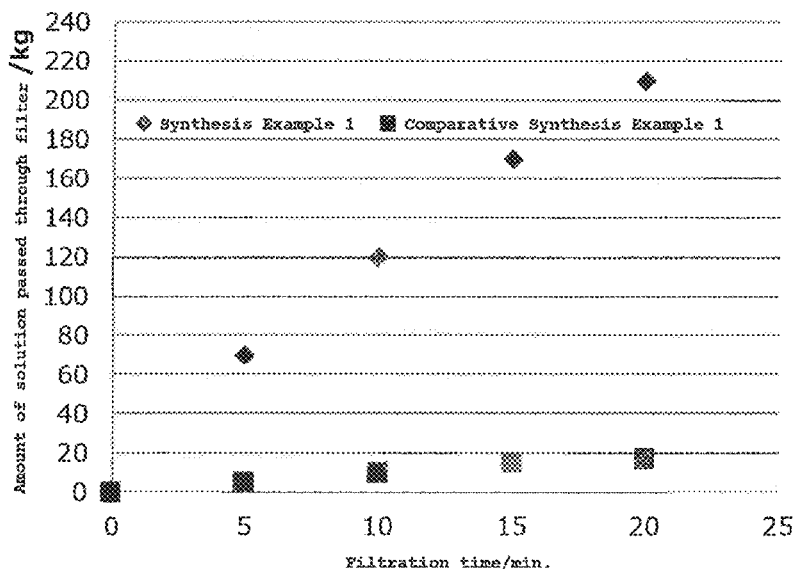
[FIG. 2]
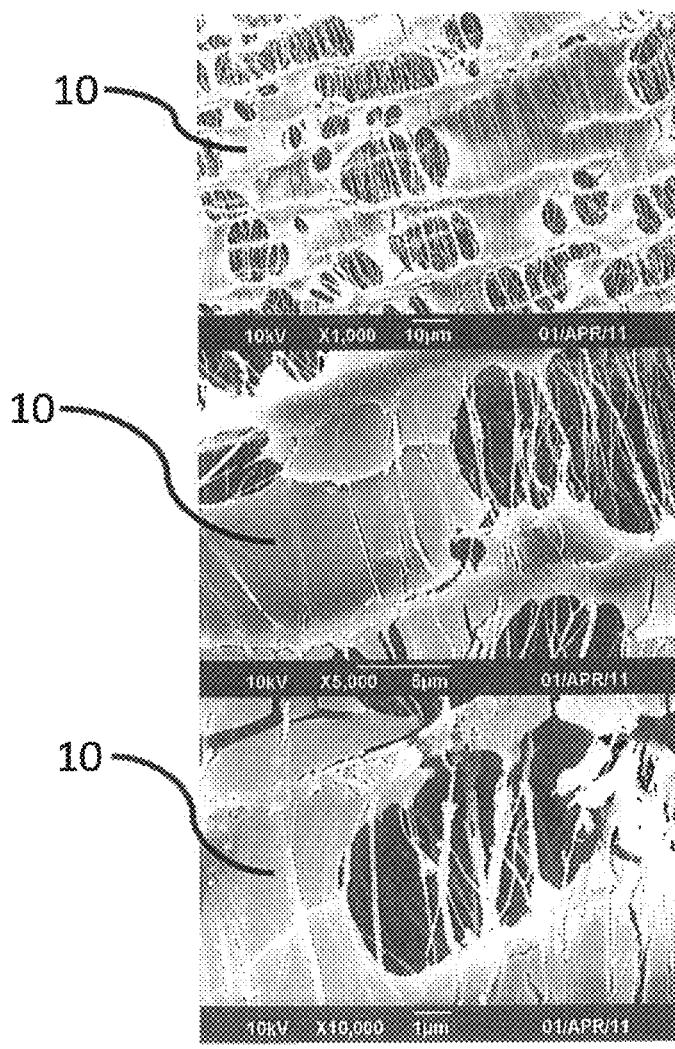

METHOD FOR PRODUCING DIHYDROXYNAPHTHALENE CONDENSATE AND DIHYDROXYNAPHTHALENE CONDENSATE

TECHNICAL FIELD

The present invention relates to a method for producing a dihydroxynaphthalene condensate and a dihydroxynaphthalene condensate applicable to a coating-type organic underlayer film used for microfabrication in processes of manufacturing for example, semiconductor elements, and the like.

BACKGROUND ART

Recently, along with advancements toward higher integration and higher speed in LSI (large scale integration), a finer pattern rule has been required. In this situation, various techniques have been developed in regard to how patterning process can be performed more finely and precisely with light sources used in lithography with light exposure, which is a commonly-employed technique at present.

Due to such processing line width reduction, phenomena have been reported in which an underlayer film is twisted and/or curved when a substrate to be processed is dry-etched using a mask that is a hard mask mainly containing carbon (Non Patent Literature 1). When such a hard mask is an amorphous carbon (hereinafter CVD-C) film prepared by CVD (chemical vapor deposition) or ALD (atomic layer deposition), the amount of hydrogen atoms in the film can be reduced quite small, and this film is generally well known to be very effective in preventing the twisting.

Nevertheless, when a substrate to be processed has a step(s), if the substrate to be processed is subjected to the subsequent patterning process by lithography in the presence of the step(s), the process margin such as depth of focus in the lithography process becomes insufficient. For this reason, the step(s) of the substrate to be processed need to be planarized with an underlayer film. Planarizing the substrate to be processed using an underlayer film reduces fluctuation in film thickness of a middle layer and a photoresist formed thereon, increases the depth of focus in lithography and can increase the process margin.

Meanwhile, the CVD-C film using a methane gas, an ethane gas, an acetylene gas, or the like as the raw material is an excellent film for forming an underlayer film having a uniform thickness on a substrate. However, in the case where the substrate has a step(s) thereon, if film thickness does not vary according to the depth of the step to be processed, an underlayer film having a flat surface cannot be formed. Hence, such CVD-C film is not suitable as means for planarizing a stepped substrate.

In such a case, when an organic underlayer film is formed by spin coating a material for forming an underlayer film containing an organic resin, there are advantages not only that the material for forming an underlayer film can fill a step(s) of the substrate, but also that the substrate surface can be planarized. Although such an organic underlayer film has been conventionally utilized as an organic hard mask and an underlayer film in a multilayer resist process, since an organic matter is used as the base material, the anti-twisting property is insufficient in forming a fine pattern in comparison with a CVD-C film. Hence, there are demands for an organic resin for an organic underlayer film having filling and planarizing properties as an organic hard mask and also having twisting resistance equivalent to a CVD-C film.

Against this background, dihydroxynaphthalene condensate has been found as an organic resin for an organic underlayer film having filling and planarizing properties as an organic hard mask and also having twisting resistance equivalent to a CVD-C film.

Dihydroxynaphthalene (1) is generally produced by the following method in an industrial scale. Specifically, the starting material naphthalene (1-1) is sulfonated to form a sulfonic acid compound (1-2). Then, this compound is converted to have hydroxyl groups by alkali fusion, so that the dihydroxynaphthalene (1) is obtained.

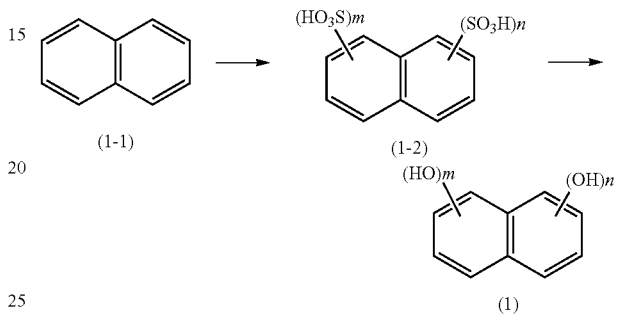

In the formulae, "n" and "m" represent integers satisfying $0 \leq m \leq 2$, $0 \leq n \leq 2$, and $m+n=2$.

In this production process, the sulfonic acid compound (1-2) is not completely consumed by the alkali fusion. As a sulfur element content among the constituents elements, the sulfonic acid compound (1-2) in an amount of approximately several hundred ppm to several thousand ppm in terms of mass remains in the dihydroxynaphthalene (1) of general industrial grades (hereinafter, the sulfonic acid compound is also referred to as "sulfur content"). Heretofore, industrial-grade dihydroxynaphthalenes containing such impurities have been mainly used as dyes. Hence, such impurities have not brought about any problems.

Generally, when a composition for forming an organic film for manufacturing a semiconductor device is used in the process of manufacturing a semiconductor device, the composition has to be purified by precise filtration using a filter having fine openings so as to eliminate defect in coating film or defect after dry etching. If this purification operation is insufficient, an electronic circuit in the semiconductor device malfunctions due to the defect in coating film or defect after dry etching, and the yield in manufacturing a semiconductor device is decreased. To prevent such a yield decrease in manufacturing a semiconductor device, the difference in the hydraulic pressure of the composition before and after the filter needs to be precisely controlled for the precise filtration.

When a dihydroxynaphthalene resin produced by using conventionally known industrial-grade dihydroxynaphthalene as the starting material is used to produce a composition for forming an organic film for manufacturing a semiconductor device, clogging occurs in the purification step by precise filtration with a fine filter having openings of 20 nm or less, which is essential for the most advanced processing material for manufacturing a semiconductor device. Hence, it has been difficult to adopt the resin as the processing material for manufacturing a semiconductor device.

Such a dihydroxynaphthalene resin presumably contains hard foreign matters (hereinafter referred to as hard particles) and soft foreign matters (hereinafter referred to as soft particles) which are deformable by a weak force due to solvent incorporation. To adopt such a dihydroxynaphthalene resin solution or a composition containing this resin (hereinafter referred to as dihydroxynaphthalene composition) as a composition for manufacturing a semiconductor device, purification with a fine filter is necessary. For example, when precise filtration is carried out using a fine filter for the purification by removing hard particles in a dihydroxynaphthalene compos the hard particles can be captured on the filter surface. Even when the hard particles are captured on the filter surface, the passage amount during the filtration hardly changes owing to gaps among the hard particles, so that the ability to purify the dihydroxynaphthalene resin composition is maintained. Meanwhile, once soft particles in the composition are captured on the filter surface, the soft particles are deformed in accordance with the flow of the composition. Eventually, gaps among the soft particles disappear, making it difficult for the composition to pass through the filter. Hence, the ability to purify the composition is decreased. When this condition further continues, the filter consequently clogs, and the filter needs to be replaced. When such filter replacement is repeated, filters for producing such a composition are consumed in uneconomically large quantities.

In this event, when the difference in the hydraulic pressure before and after the filter is set greater than 50 KPa in order to guarantee the passage amount of the composition, foreign matters, particularly soft particles, which ought to be captured by the filter, pass through pores of the filter and enter the filtrate side by the pressure difference. Thereby, the purification by filtration becomes insufficient. This causes a large number of defects in coating or after etching, decreasing the yield in manufacturing a semiconductor device.

CITATION LIST

Non-Patent Literature

Non Patent Literature 1: Proc. of Symp. Dry. Process, (2005) p. 11

SUMMARY OF INVENTION

Technical Problem

The present invention has been made in view of the above problems. An object of the present invention is to provide a dihydroxynaphthalene condensate which suppresses soft particle generation and is suitably usable for a composition excellent in filterability, and a method for producing the dihydroxynaphthalene condensate.

Solution to Problem

To accomplish the above object, the present invention provide a method for producing a dihydroxynaphthalene condensate, wherein
dihydroxynaphthalene to be used has a sulfur element content of 100 ppm or less in terms of mass among constituent elements, and
the dihydroxynaphthalene and a condensation agent are condensed in presence of an acid or a base to produce the dihydroxynaphthalene condensate.
The inventive method for producing a dihydroxynaphthalene condensate makes is possible to produce a dihydroxynaphthalene condensate which suppresses soft particle generation and is suitably usable for a composition excellent in filterability.

The condensation agent is preferably used in an amount of 0.01 to 5.0 moles relative to mole of the dihydroxynaphthalene.

When such an amount of the condensation agent is used, a dihydroxynaphthalene condensate which suppresses soft particle generation and is suitably usable for a composition excellent in filterability can be produced more reliably.

Preferably, 1,5-dihydroxynaphthalene or 2,7-dihydroxynaphthalene is used as the dihydroxynaphthalene.

In the inventive method for producing a dihydroxynaphthalene condensate, such dihydroxynaphthalenes can be used, for example.

Further, the dihydroxynaphthalene to be used preferably has a sulfur element content of 50 ppm or less in terms of mass among the constituent elements.

With such a sulfur element content adopted, a composition using this purified dihydroxynaphthalene is more reliably subjected to purification by precise filtration with a filter having openings of 20 nm or less, which essential for the most advanced processing material for manufacturing a semiconductor device.

The condensation agent to be used is preferably formaldehyde, paraformaldehyde, acetaldehyde, benzaldehyde, hydroxybenzaldehyde, or hydroxynaphthaldehyde.

The use of these aldehydes as the condensation agent enables more reliable production of a dihydroxynaphthalene condensate which suppresses soft particle generation and is suitably usable for a composition excellent in filterability.

In addition, the present invention provides a dihydroxynaphthalene condensate which is a condensate of dihydroxynaphthalene and a condensation agent, wherein a sulfur element content among constituent elements contained in the dihydroxynaphthalene condensate is 100 ppm or less in terms of mass.

The inventive dihydroxynaphthalene condensate suppresses soft particle generation and is suitably usable for a composition excellent in filterability.

The dihydroxynaphthalene condensate preferably has a weight average molecular weight of 500 to 500,000.

Such a dihydroxynaphthalene condensate is excellent in coatability, curability, and flowability.

The dihydroxynaphthalene is preferably 1,5-dihydroxynaphthalene or 2,7-dihydroxynaphthalene.

The inventive dihydroxynaphthalene condensate can be condensation products of such dihydroxynaphthalenes, for example.

The condensation agent is preferably formaldehyde, paraformaldehyde, acetaldehyde, benzaldehyde, hydroxybenzaldehyde, or hydroxynaphthaldehyde.

The dihydroxynaphthalene condensates using such condensation agents surely suppress soft particle generation and are suitably usable for a composition excellent in filterability.

Advantageous Effects of Invention

As described above, the inventive method for producing a dihydroxynaphthalene condensate makes possible to produce a dihydroxynaphthalene condensate which suppresses soft particle generation and is suitably usable for a composition with excellent filterability. Moreover, the inventive dihydroxynaphthalene condensate is capable of suppressing soft particle formation and suitably usable for a composition excellent in filterability. Further, the inventive dihydroxynaphthalene condensate is capable of forming an organic under layer film which has high pattern-curving resistance when a pattern is formed, and which prevents a high-aspect line pattern particularly finer than 40 nm from line collapse and twisting after dry etching.

BRIEF DESCRIPTION OF DRAWINGS

FIG. 1 is a graph in which amounts of polymers, which were produced in Synthesis Example 1 and Comparative Synthesis Example filtered through a filter over time are plotted.

FIG. 2 shows photographs of observing the filter with SEM after the filtration of the polymer produced in Comparative Synthesis Example 1.

DESCRIPTION OF EMBODIMENTS

As has been described above, there have been demands for developments of a dihydroxynaphthalene condensate which suppresses soft particle generation and is suitably usable for a composition excellent in filterability, and a method for producing the dihydroxynaphthalene condensate.

As described above, if a composition for forming an organic film contains soft particles, the soft particles decrease the productivity in the process of producing the composition for forming an organic or decrease the yield of the semiconductor manufacturing apparatus in some cases. Thus, soft particle generation needs to be prevented.

Hence, the present inventors have earnestly studied to achieve the above-described object and consequently found that when a condensate is produced after purification such that the amount of a sulfonic acid compound contained in a starting material dihydroxynaphthalene, that is, the sulfur element content among constituents elements, is 100 ppm or less in terms of mass, purification is possible by precise filtration with a filter having openings of 20 nm or less, which is essential for the most advanced processing material for manufacturing a semiconductor device. This finding has led to the completion of the present invention.

Specifically, the present invention is a method for producing a dihydroxynaphthalene condensate, wherein dihydroxynaphthalene to be used has a sulfur element content of 100 ppm or less in terms of mass among constituent elements, and the dihydroxynaphthalene and a condensation agent are condensed in presence of an acid or a base to produce the dihydroxynaphthalene condensate.

Hereinafter, embodiments of the present invention will be described in detail. However, the present invention is not limited thereto.

[Dihydroxynaphthalene Condensate]

A dihydroxynaphthalene condensate of the present invention is a condensate of dihydroxynaphthalene and a condensation agent. The sulfur element content among constituent elements contained in the dihydroxynaphthalene condensate is 100 ppm or less in terms of mass.

(Dihydroxynaphthalene)

A raw material of the inventive hydroxynaphthalene condensate is dihydroxynaphthalene shown by the following general formula (1).

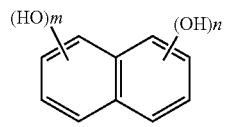

In the formula, "n" and "m" represent integers satisfying 0≤m≤2, 0≤n≤2, and m+n=2.

Here, the dihydroxynaphthalene represented by the general formula (1) is not particularly limited. Examples thereof include 1,2-dihydroxynaphthalene, 2,3-dihydroxynaphthalene, 2,3-dihydroxynaphthalene, 1,4-dihydroxynaphthalene, 1,5-dihydroxynaphthalene, 1,6-dihydroxynaphthalene, 2,6-dihydroxynaphthalene, 1,7-dihydroxynaphthalene, 2,7-dihydroxynaphthalene, 1,8-dihydroxynaphthalene, and the like. The dihydroxynaphthalene is particularly preferably 1,5-dihydroxynaphthalene or 2,7-dihydroxynaphthalene.

As described above, the dihydroxynaphthalene (1) is industrially produced by the following method in general. Specifically, the starting material naphthalene (1-1) is sulfonated to obtain the sulfonic acid compound (1-2). Then, this compound is converted to have hydroxyl groups by alkali fusion, so that the dihydroxynaphthalene (1) is obtained.

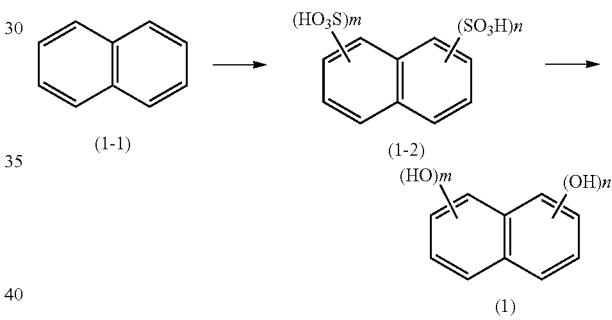

In the formulae, "m" and "n" are as defined above.

In this event, the sulfonic acid compound (1-2) is not completely consumed by the alkali fusion. As the sulfur element content among the constituents elements, the sulfonic acid compound (1-2) remains in an amount of approximately several hundred ppm to several thousand ppm in terms of mass in the dihydroxynaphthalene (1) of general industrial grades. Table 1 below shows contents, in terms of mass, of sulfur elements contained in dihydroxynaphthalenes of general industrial grades.

TABLE 1

| | Company A-1 | Company A-2 | Company A-3 | Company B-1 | Company B-2 | Company C-1 | Company C-2 | Company C-3 |
|---|---|---|---|---|---|---|---|---|
| Sulfur element content/ppm | 1390 | 5300 | 260 | 1390 | 5300 | 260 | 260 | 300 |

Note that, as the method for quantifying the sulfur element in the dihydroxynaphthalene (1), there are known a combination method of sample combustion and titration, a combination method of sample combustion and ion chromatography, inductively coupled plasma emission spectroscopy (ICP-AES/OES), and the like. The method for quantifying the sulfur element in the dihydroxynaphthalene after impurity removal is preferably ICP-AES/OES which is more highly sensitive.

The inventive dihydroxynaphthalene condensate has a sulfur element content of 100 ppm or less in terms of mass among the constituent elements. When the dihydroxynaphthalene to be used has a sulfur element content of 100 ppm or less in terms of mass among the constituent elements, the sulfur element in the inventive dihydroxynaphthalene condensate can be 100 ppm or less in terms of mass. The dihydroxynaphthalene to be used more preferably has a sulfur element content of 50 ppm or less in terms of mass.

The method for removing a sulfonic acid compound (sulfur content) from dihydroxynaphthalene of general industrial grades containing several hundred ppm to several thousand ppm of the sulfonic acid compound includes a method involving dissolving dihydroxynaphthalene into an organic solvent and washing the resultant with an aqueous alkaline solution, followed by liquid separation; a method involving removing a sulfonic acid compound by an adsorption treatment with an adsorbent such as activated carbon, silica gel, or alumina; and the like. Among these, the method involving the adsorbent treatment is preferable, and the adsorption treatment with neutral alumina is particularly preferable. A mixture of these adsorbents may be used.

In the particle size distribution of the neutral alumina used in this event, preferably, particles of 63 μm to 250 μm account for 80% or more, and particles of less than 63 μm account for less than 10%. More preferably, particles of less than 60 μm account for less than 5% so as to facilitate the process of removing the adsorbent after the adsorption.

(Condensation Agent)

The condensation agent of the inventive hydroxynaphthalene condensate is not particularly limited. Examples thereof include formaldehyde, trioxane, paraformaldehyde, acetaldehyde, propylaldehyde, adamantanecarbaldehyde, benzaldehyde, hydroxybenzaldehyde, phenylacetaldehyde, α-phenylpropylaldehyde, β-phenylpropylaldehyde, o-chlorobenzaldehyde, m-chlorobenzaldehyde, p-chlorobenzaldehyde, o-nitrobenzaldehyde, m-nitrobenzaldehyde, p-nitrobenzaldehyde, o-methylbenzaldehyde, m-methylbenzaldehyde, p-methylbenzaldehyde, p-ethylbenzaldehyde, p-n-butylbenzaldehyde, 1-naphthylaldehyde, 2-naphthylaldehyde, 6-hydroxy-2-naphthylaldehyde, anthracenecarbaldehyde, pyrenecarbaldehyde, furfural, methylal, and the like. Preferable examples include formaldehyde and paraformaldehyde.

As the ratio between the dihydroxynaphthalene and the condensation agent, the condensation agent is preferably 0.01 to 5.0 moles, more preferably 0.05 to 2.0 moles, relative to 1 mole of the dihydroxynaphthalene.

As the molecular weight of the inventive dihydroxynaphthalene condensate in terms of polystyrene, the weight average molecular weight (Mw) is preferably 500 to 500,000, more preferably 1,000 to 100,000, further preferably 1,000 to 10,000, and particularly preferably 2,000 to 6,000. The use of the dihydroxynaphthalene condensate having such a weight average molecular weight results in the composition more excellent in coatability, curability, and flowability. Moreover, the molecular weight dispersity is preferably within a range of 1.2 to 20.

The present invention is preferably a dihydroxynaphthalene condensate which is a condensate of, particularly, 1,5-dihydroxynaphthalene or 2,7-dihydroxynaphthalene and formaldehyde, paraformaldehyde, hydroxybenzaldehyde, or hydroxynaphthaldehyde. Such a dihydroxynaphthalene condensate is a material surely subjected to purification by precise filtration with a filter having openings of 20 nm or less, which is essential for the most advanced processing material for manufacturing a semiconductor device. Besides, the dihydroxynaphthalene condensate is capable of forming an organic underlayer film which prevents line collapse and twisting after dry etching in a high-aspect line pattern finer than 40 nm.

Such an inventive dihydroxynaphthalene condensate suppresses soft particle generation and is suitably usable for a composition excellent in filterability. In addition, the inventive dihydroxynaphthalene condensate makes it possible to form an organic underlayer film which has high pattern-curving resistance in forming a pattern, and which prevents a high-aspect line pattern particularly finer than 40 nm from line collapse and twisting after dry etching.

[Method for Producing Dihydroxynaphthalene Condensate]

Moreover, the present invention provides a method for producing a dihydroxynaphthalene condensate, wherein dihydroxynaphthalene to be used has a sulfur element content of 100 ppm or less in terms of mass among constituent elements, and the dihydroxynaphthalene and a condensation agent are condensed in presence of an acid or a base to produce the dihydroxynaphthalene condensate.

(Dihydroxynaphthalene)

As the dihydroxynaphthalene used in the inventive method for producing a dihydroxynaphthalene condensate, the above-described dihydroxynaphthalene can be used which has a sulfur element content of 100 ppm or less in terms of mass among constituent elements.

The method for purifying the raw material to obtain such dihydroxynaphthalene having a sulfur element content of 100 ppm or less in terms of mass among constituent elements includes the following method.

In order to remove a sulfonic acid compound which is an impurity contained in industrial-grade dihydroxynaphthalene, an adsorption treatment with neutral alumina is preferable. When the adsorption treatment is performed with neutral alumina, an adsorbent other than the neutral alumina may be mixed for use, such as activated carbon, acidic alumina, or basic alumina.

The neutral alumina used in this event is preferably granules whose hue is pale yellow to white, more preferably white granules. Moreover, the aluminum oxide purity is preferably 85% or more, more preferably 94.0% or more. The ignition loss of the adsorbent portion is preferably 8% or less, more preferably 5.5% or less. The adsorbent has a bulk density of preferably 8 to 20 ml/10 g, more preferably 12 to 16 ml/10 g. Further, the activated alumina has a pH of preferably 6.5 to 8.5, more preferably 7.0 to 8.0.

The particle size distribution of the neutral alumina used as the adsorbent is as described above; preferably, particles of 63 μm to 250 μm account for 80% or more, while particles of less than 63 μm account for less than 10%. More preferably, particles of less than 60 μm account for less than 5% to facilitate the process of removing the neutral alumina after the adsorption.

Moreover, the method for using the neutral alumina as the adsorbent is not particularly limited. In a preferable method, for example, the dihydroxynaphthalene is dissolved into an organic solvent, the neutral alumina is added as the adsorbent to the solution and stirred, and the neutral alumina is separated by filtration.

In this event, the organic solvent for dissolving the dihydroxynaphthalene is not particularly limited. Examples thereof include alcohols such as methanol, ethanol, propanol, propylene glycol methyl ether, methyl cellosolve, and ethyl cellosolve; ketones such as methyl ethyl ketone, methyl isobutyl ketone, methyl amyl ketone, and cyclohexanone; esters such as ethyl acetate, propylene glycol methyl ether acetate, and γ-butyrolactone; aliphatic hydrocarbons such as pentane and hexane; aromatic hydrocarbons such as toluene and xylene; ethers such as tetrahydrofuran and dioxane; and the like.

The neutral alumina is preferably added in an amount of 5 parts by mass or more relative to 100 parts by mass of the dihydroxynaphthalene. When such an amount of the neutral alumina is added, the sulfur content in the dihydroxynaphthalene can be surely removed. Although the upper limit is not particularly limited, it is not economical to use the neutral alumina in a large amount. Thus, the use of 100 parts by mass of the neutral alumina is sufficient.

In the above-described method, after the neutral alumina is added, the solution is stirred at a temperature of preferably 0 to 150° C. Moreover, the stirring time is preferably 0.1 hours or more. The upper limit of the stirring time is not particularly limited, and the stirring for 20 hours is sufficient.
(Condensation Agent)

As the condensation agent used in the inventive method for producing a dihydroxynaphthalene condensate, those described as above can be used.
(Condensation Reaction Method)

The polycondensation reaction using the raw materials as described above can be performed normally without a solvent or in a solvent using an acid or a base as a catalyst at room temperature or if necessary under cooling or heating.

The solvent used is not particularly limited, and includes alcohols such as methanol, ethanol, isopropyl alcohol, butanol, ethylene glycol, propylene glycol, diethylene glycol, glycerol, methyl cellosolve, ethyl cellosolve, butyl cellosolve, and propylene glycol monomethyl ether; ethers such as diethyl ether, dibutyl ether, diethylene glycol diethyl ether, diethylene glycol dimethyl ether, tetrahydrofuran, and 1,4-dioxane; chlorinated solvents such as methylene chloride, chloroform, dichloroethane, and trichloroethylene; hydrocarbons such as hexane, heptane, benzene, toluene, xylene, and cumene; nitriles such as acetonitrile; ketones such as acetone, ethyl methyl ketone, and isobutyl methyl ketone; esters such as ethyl acetate, n-butyl acetate, and propylene glycol methyl ether acetate; lactones such as γ-butyrolactone; and non-protic polar solvents such as dimethyl sulfoxide, N,N-dimethyl formamide, and hexamethyl phosphoric triamide. These can be used alone or in a mixture of two or more kinds. These solvents can be used within a range of 0 to 2,000 parts by mass relative to 100 parts by mass of the reaction raw materials.

The acid catalyst to be used is not particularly limited, and includes inorganic acids such as hydrochloric acid, hydrobromic acid, sulfuric acid, nitric acid, phosphoric acid, and heteropoly acid; organic acids such as oxalic acid, trifluoroacetic acid, methanesulfonic acid, benzenesulfonic acid, p-toluenesulfonic acid, and trifluoromethanesulfonic acid; and Lewis acids such as aluminum trichloride, aluminum ethoxide, aluminum isopropoxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium (IV) ethoxide, titanium(IV) isopropoxide, and titanium(IV) oxide. Among these, p-toluenesulfonic acid is preferable.

The base catalyst to be used is not particularly limited, and includes inorganic bases such as sodium hydroxide, potassium hydroxide, barium hydroxide, sodium carbonate, sodium hydrogen carbonate, potassium carbonate, lithium hydride, sodium hydride, potassium hydride, and calcium hydride; alkyl metals such as methyl lithium, n-butyl lithium, methyl magnesium chloride, and ethyl magnesium bromide; alkoxides such as sodium methoxide, sodium ethoxide, and potassium t-butoxide; and organic bases such as triethylamine, diisopropyl ethyl amine, N,N-dimethylaniline, pyridine, and 4-dimethylaminopyridine.

The amount of the catalyst used is within a range of preferably 0.001 to 100 weight %, more preferably 0.005 to 50 weight %, relative to the raw materials. The reaction temperature is preferably about −50° C. to the boiling point of the solvent, more preferably room temperature to 100° C.

The polycondensation reaction method includes: a method in which the dihydroxynaphthalene, the condensation agent, and the catalyst are charged at once; a method in which the condensation agent is added dropwise to a mixed solution of the catalyst and the dihydroxynaphthalene; a method in which the catalyst is added dropwise to a mixture of the dihydroxynaphthalene and the condensation agent; and the like.

The method for separating the condensate after completion of the polycondensation reaction includes: a method in which an unreacted raw material, catalyst, and so forth present in the system are removed by adding an appropriate solvent and water to fractionate the condensate; a method in which the condensate is dissolved in a good solvent and then reprecipitated in a poor solvent; and the like. These methods can be selected depending on the properties of the obtained reaction product.

Such an inventive method for producing a dihydroxynaphthalene condensate makes it possible to produce a dihydroxynaphthalene condensate which suppresses soft particle generation and is suitably usable for a composition excellent in filterability. Moreover, the inventive method makes it possible to produce a dihydroxynaphthalene condensate suitably usable for an organic underlayer film which has high pattern-curving resistance in forming a pattern, and which prevents a high-aspect line pattern particularly finer than 40 nm from line collapse and twisting after dry etching.

EXAMPLE

Hereinafter, the present invention will be specifically described by referring to Synthesis Example, Comparative Synthesis Example, Examples, and Comparative Examples. However, the present invention is not limited to these descriptions. Note that, as molecular weights, weight average molecular weight (Mw) and number average molecular weight (Mn) were measured in terms of polystyrene by gel permeation chromatography (GPC). Then, the dispersity (Mw/Mn) was calculated therefrom.

Synthesis Example 1

In a solvent mixture containing 127.6 g of propylene glycol methyl ether (hereinafter, PGME) and 353.6 g of methyl isobutyl ketone (hereinafter, MIBK), 72.2 g of commercially available 1,5-dihydroxynaphthalene (hereinafter, 15DHN, sulfur element content: 400 ppm, measured by ICP-OES) was dissolved. To this, 57.2 g of neutral alumina (manufactured by Tomita Pharmaceutical Co., Ltd., Tomita-AD-250NS, particle diameters: 60 to 250 μm, pH: 7.5) was added and stirred at room temperature for 12 hours. Then, the neutral alumina was separated by filtration, and the resulting 15DHN solution in PGME/MIBK was washed with ion-exchanged water. PGME was further added and concentrated. Thus, 500 g of a 13 wt % 15DHN-PGME solution was obtained. The sulfur element content in the solid content of this 15DHN solution was measured by ICP-OES and found to be 45 ppm.

Next, in a 1000-ml flask, 500 g (0.5 moles) of the 13 wt % 15DHN-PGME solution was mixed with 2.8 g of p-toluenesulfonic acid and 2.8 g of PGME. While the mixture was being stirred at 80° C., 14.3 g of a 50 wt % formaldehyde aqueous solution was added thereto. With the temperature kept at 80° C., the stirring continued for 6 hours. Then, the temperature was cooled to room temperature (monomer conversion ratio: 77%). The resulting solution was concentrated under reduced pressure. Subsequently, 540 g of hexane was added thereto, and the polymer content was separated and precipitated. The upper filtrate was separated by filtration and removed. Thereafter, this operation was repeated, so that the residual monomer content was 5% or less. The remaining polymer content was dissolved again in 200 g of MIBK, 200 g of ion-exchanged water was added thereto, and the metal ion content was removed. To the MIRK solution from which the metal ion content had been removed, 300 g of propylene glycol monomethyl ether acetate (PGMEA) was added and concentrated under reduced pressure. Thus, a PGMEA solution containing approximately 20 wt % of a polymer 1 as shown by the following formula was obtained. The molecular weight (Mw) and the dispersity (Mw/Mn) of the obtained polymer in terms of polystyrene were measured by gel permeation chromatography (GPC). The sulfur element content was measured by ICP-OES. As a result, the molecular weight (Mw) was 3,500, the dispersity (Mw/Mn) was 2.01, and the sulfur element content in the solid content was 45 ppm.

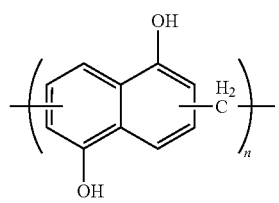

Polymer 1

In the formula, "n" represents the number of repeating units next to it, ranging from 2 to 100.

Comparative Synthesis Example 1

A comparative polymer 1 was obtained according to the same reactions in Synthesis Example 1, except that the commercially available 15DHN was not treated with the neutral alumina but was used for the polymerization reaction. The molecular weight (Mw) and the dispersity (Mw/Mn) of the obtained comparative polymer 1 in terms of polystyrene were measured by gel permeation chromatography (GPC). The sulfur element content was measured by ICP-OES. As a result, the molecular weight (Mw) was 3,600, the dispersity (Mw/Mn) was 2.03, and the sulfur element content was 435 ppm.

[Method for Measuring Sulfur Element Content by ICP-OES]

(Pretreatment: Microwave Digestion Method)

These samples were pretreated for ICP-OES by using a microwave sample digestion system (MULTIWAVE 3000 manufactured by Anton Paar GmbH). 0.5 g of each sample and 10 ml of 69.0% nitric acid (Ultrapur-100 manufactured by Kanto Chemical Co., Inc.) were put into a PTFE (polytetrafluoroethylene) digestion container and left standing for 1 hour. Then, microwave digestion was carried out with this system for 35 minutes. After the digestion, the solution was transferred to a TPX storage container and diluted with distilled water such that the total amount became 50 g. Thus, 100-fold diluted samples were prepared.

(ICP-OES Measurement)

The analysis of the sulfur element content by ICP-OES was conducted with a CID/ICP emission spectrometer (iCAP6000DUO manufactured by Thermo Fisher SCIENTIFIC Inc.). The pretreated 100-fold diluted samples described above were measured under the following setting conditions.

(ICP-OES Setting Conditions)
  High-frequency output: 1150 W
  Plasma gas flow rate: 12.0 L/min
  Auxiliary gas flow rate: 0.5 L/min
  Nebulizer gas flow rate: 0.5 L/min
  Peristaltic pump rotational speed: 50 rpm
  Measurement direction: axial
  Analysis integration times (low wavelength/high wavelength): 10 seconds/10 seconds
  The number of analysis integrations: 3 times
  Sample replacement time: 30 seconds

[Polymer (Condensate) Filtration Study 1]

PGMEA solutions containing 20 mass % of the polymer (neutral alumina-treated product) obtained in Synthesis Example 1 or the comparative polymer 1 (neutral alumina-untreated product) obtained in Comparative Synthesis Example 1 were prepared and filtered through a 10-inch (250 mm) PTFE filter having 0.1-μm openings. The relationship between the filtration time and the weight of the solution passed was as shown in FIG. 1. It was verified that the filterability of the comparative polymer 1 was significantly poor while the filterability of the polymer 1 was favorable.

In addition, the top of the filter where the comparative polymer 1 was poorly filtered was observed with SEM. It was found as shown in FIG. 2 that a component of a viscous material 1.0 (soft particles) adhered on the filter.

In the comparative polymer 1, sulfonic acid impurities as shown below were presumably incorporated into the polymer, thereby forming the deposit which deteriorated the filterability.

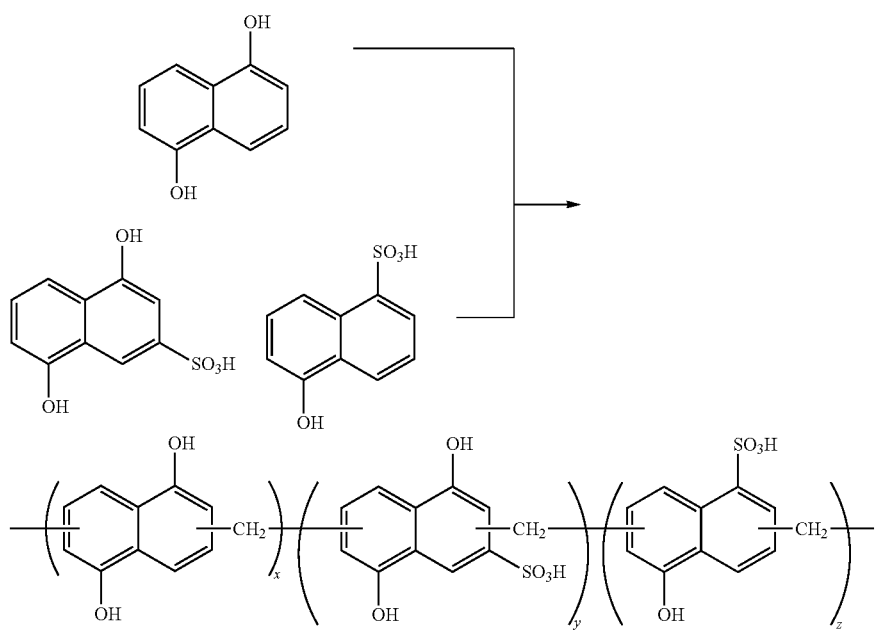

In the formula, "x", "y", and "z" each represent the number of repeating units. x+y+z ranges from 2 to 100.

[Polymer (Condensate) Filtration Study 2]

PGMEA solutions containing 20 mass % of the polymer 1 (neutral alumina-treated product) obtained in Synthesis Example 1 or the comparative polymer 1 (neutral alumina-untreated product) obtained in Comparative Synthesis Example 1 were prepared and filtered through a nylon filter having 20-nm openings. The polymer 1 was successfully filtered at the filtration pressure of 50 kPa. In contrast, the filter was clogged with the comparative polymer 1. Even when the pressure was increased to 500 kPa, no filtrate was obtained.

From the foregoing, in Synthesis Example 1 using the dihydroxynaphthalene having a sulfur element content of 100 ppm or less in terms of mass, the filterability was favorable. In contrast, the polymer using the dihydroxynaphthalene from which the sulfur content had not been removed as in Comparative Synthesis Example 1 had poor filterability.

[Preparation of Composition for Forming Organic Underlayer Film (Dihydroxynaphthalene Composition)]

The polymer 1, the comparative polymer 1, and various additives were blended into compositions shown in Table 2 below (the units in the parentheses are kilogram), and filtered through a nylon filter having a 10 inch size with 20-nm openings by using a production facility for a composition for forming an organic underlayer film. Thus, compositions for forming an organic underlayer film were produced (SOL-1, -2, comparative SOL-1, -2).

TABLE 2

| SOL | Polymer (kg) | Cross-linking agent (kg) | Acid generator (kg) | Surfactant (kg) | Solvent (kg) |
|---|---|---|---|---|---|
| SOL-1 | polymer 1 (1) | — | — | SF1 (0.005) | PGMEA (25) |

TABLE 2-continued

| SOL | Polymer (kg) | Cross-linking agent (kg) | Acid generator (kg) | Surfactant (kg) | Solvent (kg) |
|---|---|---|---|---|---|
| SOL-2 | polymer 1 (1) | CL1 (0.1) | AG1 (0.01) | SF1 (0.005) | PGMEA (25) |
| comparative SOL-1 | comparative polymer 1 (1) | — | — | SF1 (0.5) | PGMEA (25) |
| comparative SOL-2 | comparative polymer 1 (1) | CL1 (0.1) | AG1 (0.01) | SF1 (0.005) | PGMEA (25) |

The crosslinking agent CL1, the acid generator AG1, and the surfactant SF1 used were as follows.

SF1: FC-4430 manufactured by 3M

AG1

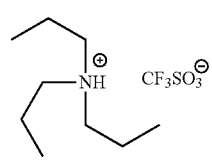

CL1

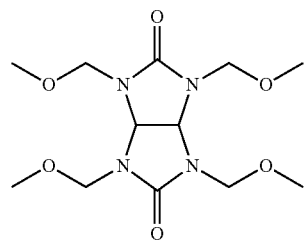

The flow speeds during the filtration with the filter and the pressure differences between before and after the filter are shown in Table 3.

TABLE 3

| Composition | SOL | Sulfur content in condensate | Flow speed during filtration | Pressure difference between before and after filter |
|---|---|---|---|---|
| UL1-1 | SOL-1 | 45 ppm | 300 g/min. | 11 KPa |
| UL1-2 | SOL-1 | 45 ppm | 800 g/min. | 30 KPa |
| UL2-1 | SOL-2 | 45 ppm | 300 g/min. | 10 KPa |
| UL2-2 | SOL-2 | 45 ppm | 800 g/min. | 29 KPa |
| comparative UL1-1 | comparative SOL-1 | 435 ppm | 300 g/min. | 40 KPa |
| comparative UL1-2 | comparative SOL-1 | 435 ppm | 800 g/min. | 100 KPa |
| comparative UL2-1 | comparative SOL-2 | 435 ppm | 300 g/min. | 39 KPa |
| comparative UL2-2 | comparative SOL-2 | 435 ppm | 800 g/min. | 100 KPa |

Each of the obtained compositions for forming an organic underlayer film was connected to Clean Track ACT12 manufactured by Tokyo Electron Limited, and applied onto a 12-inch (diameter: 300 mm) silicon wafer with no filter being connected to the connection pipe. The resultant was baked at 250° C. for 60 seconds to prepare a coating film. A defect with a size of 60 nm or more on the coating film was checked by defect inspection using a dark-field defect inspection system SP5 manufactured by KLA-Tencor Corporation (Examples 1 to 4, Comparative Examples 1 to 4). Table 4 shows the result.

TABLE 4

| Example | Composition | Number of defects |
|---|---|---|
| Example 1 | UL1-1 | 10 |
| Example 2 | UL1-2 | 20 |
| Example 3 | UL2-1 | 12 |
| Example 4 | UL2-2 | 26 |
| Comparative Example 1 | comparative UL1-1 | 313 |
| Comparative Example 2 | comparative UL1-2 | 538 |
| Comparative Example 3 | comparative UL2-1 | 298 |
| Comparative Example 4 | comparative UL2-2 | 657 |

These results revealed that, as in Examples 1 to 4, the use of the dihydroxynaphthalene condensate with a sulfur element content of 100 ppm or less in terms of mass reduced the number of defects in the coating film prepared from the obtained composition. In contrast, as in Comparative Examples 1 to 4, the use of the dihydroxynaphthalene condensate with a sulfur element content exceeding 100 ppm in terms of mass increased the pressure difference between before and after the filter when the composition was filtered and purified. Thus, foreign matters in the composition were hardly trapped the filter, and the inspection of the coating film prepared from the obtained composition showed a large number of defects in the coating film.

From the foregoing, it was revealed that the inventive dihydroxynaphthalene condensate suppresses soft particle generation from sulfur content and is suitably usable for a composition excellent in filterability.

It should be noted that the present invention is not restricted to the above-described embodiments. The embodiments are merely examples so that any embodiments that have substantially the same feature and demonstrate the same functions and effects as those in the technical concept as disclosed in claims of the present invention are included in the technical range of the present invention.

The invention claimed is:

1. A method for producing a dihydroxynaphthalene condensate, the method comprising:
   treating a dihydroxynaphthalene with neutral alumina particles having a particle size distribution in which 80% or more of the neutral alumina particles have a size in a range of from 63 μm to 250 μm, and less than 10% of the neutral alumina particles have a size of less than 63 μm, wherein the treated dihydroxynaphthalene has a sulfur element content of 100 ppm or less in terms of mass among constituent elements, and
   condensing the treated dihydroxynaphthalene and a condensation agent in presence of an acid or a base to produce the dihydroxynaphthalene condensate.

2. The method for producing a dihydroxynaphthalene condensate according to claim 1, wherein the condensation agent is used in an amount of 0.01 to 5.0 moles relative to 1 mole of the dihydroxynaphthalene.

3. The method for producing a dihydroxynaphthalene condensate according to claim 1, wherein the dihydroxynaphthalene is 1,5-dihydroxynaphthalene or 2,7-dihydroxynaphthalene.

4. The method for producing a dihydroxynaphthalene condensate according to claim 2, wherein the dihydroxynaphthalene is 1,5-dihydroxynaphthalene or 2,7-dihydroxynaphthalene.

5. The method for producing a dihydroxynaphthalene condensate according to claim 1, wherein the treated dihydroxynaphthalene has a sulfur element content of 50 ppm or less in terms of mass among the constituent elements.

6. The method for producing a dihydroxynaphthalene condensate according to claim 2, wherein the treated dihydroxynaphthalene has a sulfur element content of 50 ppm or less in terms of mass among the constituent elements.

7. The method for producing a dihydroxynaphthalene condensate according to claim 3, wherein the treated dihydroxynaphthalene has a sulfur element content of 50 ppm or less in terms of mass among the constituent elements.

8. The method for producing a dihydroxynaphthalene condensate according to claim 4, wherein the treated dihydroxynaphthalene has a sulfur element content of 50 ppm or less in terms of mass among the constituent elements.

9. The method for producing a dihydroxynaphthalene condensate according to claim 1, wherein the condensation agent is formaldehyde, paraformaldehyde, acetaldehyde, benzaldehyde, hydroxybenzaldehyde, or hydroxynaphthaldehyde.

10. The method for producing a dihydroxynaphthalene condensate according to claim 2, wherein the condensation agent is formaldehyde, paraformaldehyde, acetaldehyde, benzaldehyde, hydroxybenzaldehyde, or hydroxynaphthaldehyde.

11. The method for producing a dihydroxynaphthalene condensate according to claim 3, wherein the condensation agent is formaldehyde, paraformaldehyde, acetaldehyde, benzaldehyde, hydroxybenzaldehyde, or hydroxynaphthaldehyde.

12. The method for producing a dihydroxynaphthalene condensate according to claim 4, wherein the condensation agent is formaldehyde, paraformaldehyde, acetaldehyde, benzaldehyde, hydroxybenzaldehyde, or hydroxynaphthaldehyde.

13. A dihydroxynaphthalene condensate, produced by the method according to claim 1, wherein a sulfur element content among constituent elements contained in the dihydroxynaphthalene condensate is 100 ppm or less in terms of mass.

14. The dihydroxynaphthalene condensate according to claim 13, wherein the dihydroxynaphthalene condensate has a weight average molecular weight of 500 to 500,000.

15. The dihydroxynaphthalene condensate according to claim 13, wherein the dihydroxynaphthalene is 1,5-dihydroxynaphthalene or 2,7-dihydroxynaphthalene.

16. The dihydroxynaphthalene condensate according to claim 14, wherein the dihydroxynaphthalene is 1,5-dihydroxynaphthalene or 2,7-dihydroxynaphthalene.

17. The dihydroxynaphthalene condensate according to claim 13, wherein the condensation agent is formaldehyde, paraformaldehyde, acetaldehyde, benzaldehyde, hydroxybenzaldehyde, or hydroxynaphthaldehyde.

18. The dihydroxynaphthalene condensate according to claim 14, wherein the condensation agent is formaldehyde, paraformaldehyde, acetaldehyde, benzaldehyde, hydroxybenzaldehyde, or hydroxynaphthaldehyde.

19. The dihydroxynaphthalene condensate according to claim 15, wherein the condensation agent is formaldehyde, paraformaldehyde, acetaldehyde, benzaldehyde, hydroxybenzaldehyde, or hydroxynaphthaldehyde.

20. The dihydroxynaphthalene condensate according to claim 16, wherein the condensation agent is formaldehyde, paraformaldehyde, acetaldehyde, benzaldehyde, hydroxybenzaldehyde, or hydroxynaphthaldehyde.

\* \* \* \* \*